United States Patent [19]

Okushima et al.

[11] 4,213,902
[45] Jul. 22, 1980

[54] PROCESS FOR PRODUCING STEROIDAL 7α-ACYLTHIO-4-EN-3-ONES

[75] Inventors: Hiromi Okushima, Kawasaki; Issei Nitta, Machida; Rikizo Furuya, Yokohama, all of Japan

[73] Assignee: Mitsubishi Chemical Industries Ltd., Tokyo, Japan

[21] Appl. No.: 8,173

[22] Filed: Jan. 31, 1979

Related U.S. Application Data

[63] Continuation-in-part of Ser. No. 882,225, Feb. 28, 1978, abandoned.

[30] Foreign Application Priority Data

Mar. 17, 1977 [JP] Japan .................................. 52/29586

[51] Int. Cl.² .............................................. C07J 19/00
[52] U.S. Cl. ................................................. 260/239.57
[58] Field of Search ..................................... 260/239.57

[56] References Cited

U.S. PATENT DOCUMENTS

| 3,894,006 | 7/1975 | Stache et al. ................. 260/239.57 |
| 4,118,488 | 10/1978 | Philippson et al. ............. 260/239.57 |

OTHER PUBLICATIONS

Schaub et al., J. Org. Chem. 26 (1961), pp. 3915–3925.

Primary Examiner—Elbert L. Roberts
Attorney, Agent, or Firm—Oblon, Fisher, Spivak, McClelland & Maier

[57] ABSTRACT

A steroidal 7α-acylthio-4-en-3-one is produced by adding a thiocarboxylic acid to a steroidal 4,6-dien-3-one in the presence of a strong acid in a neutral organic solvent.

12 Claims, No Drawings

4,213,902

PROCESS FOR PRODUCING STEROIDAL 7α-ACYLTHIO-4-EN-3-ONES

This application is a continuation-in-part of application Ser. No. 882,225 filed Feb. 28, 1978, now abandoned.

BACKGROUND OF THE INVENTION

1. Field of the Invention

This invention relates to a process for producing steroidal 7α-acylthio-4-en-3-ones. More particularly, this invention relates to a commercially practical process for producing steroidal 7α-acylthio-4-en-3-ones such as 7α-acetylthio-17-hydroxy-3-oxo-17α-pregn-4-ene-21-carboxylic acid γ-lactone (hereinafter referred to as "spironolactone") which is a therapeutically effective antialdosteronic diuretic.

2. Description of the Prior Art

It is already known that the addition of a thiol or thiocarboxylic acid to an olefin can be accelerated with either light or a radical initiator such as a peroxide or azobisisobutyronitrile. For the addition of a thiocarboxylic acid to a steroidal 4,6-dien-3-one, however, such radical initiators have been found to exert little effect on acceleration of the reaction.

The above-mentioned spironolactone which is one of the steroidal 7α-acylthio-4-en-3-ones is usually prepared by reacting 17-hydroxy-3-oxo-17α-pregna-4,6-diene-21-carboxylic acid γ-lactone with a large excess of thioacetic acid under heating. According to this procedure, the 7β-acetylthio derivative which is therapeutically inactive is also produced as a by-product in approximately 25% yield, while the therapeutically active 7α-acetylthio derivative is obtained in a yield as low as 70%.

It is known from Japanese Patent Laying-Open Publication No. 4020/71 that the 7α-acetylthio derivative can be obtained in approximately 90% yield with methanol being used as a solvent but without the use of strong acid. In this procedure, however, 5 to 10% by-products are always formed in addition to the 7α- and 7β-acetylthio derivatives and therefore it is impossible to obtain the desired 7α-acetylthio derivative in a yield exceeding 90%.

An article by Schaub et al., J. Org. Chem., 26, 3915–3925 (1961), discloses the formation of 7α-alkylthio and 7α-acylthio steroid hormone derivatives by addition to steroidal 4,6-dien-3-ones. Some examples showed the use of HCl in glacial acetic acid, but the yields were only moderate. The best yield was 61% for the formation of 7α-acetylthiotestosterone acetate.

A need therefore continues to exist for a method of forming steroidal 7α-acylthio-4-en-3-ones in high yield without formation of side products other than the epimeric 7β-acylthio derivatives.

SUMMARY OF THE INVENTION

Accordingly, one object of this invention is to provide process suitable for commercial-scale production of steroidal 7α-acylthio-4-en-3-ones which permits the reaction rate to be increased and suppresses the formation of by-products other than the 7α- and 7β-acylthio derivatives. Another object of this invention is to increase the ratio of 7α-acylthio derivative to 7β-acylthio derivative formed so as to obtain the desired 7α-derivative in higher yields.

Briefly, these objects and other objects of the invention as hereinafter will become more readily apparent can be attained by providing a process for preparing steroidal 7α-acylthio-4-en-3-ones by the addition of a thiocarboxylic acid to a steroidal 4,6-dien-3-one, characterized by effecting the reaction in the presence of a strong acid in a neutral organic solvent.

DETAILED DESCRIPTION OF THE PREFERRED EMBODIMENTS

The steroidal 4,6-dien-3-ones which are used as starting materials for the process of this invention include 17-hydroxy-3-oxo-17α-pregna-4,6-diene-21-carboxylic acid γ-lactone, androsta-4,6-diene-3,17-dione, 17β-acetoxyandrosta-4,6-dien-3-one, 1α,2α-methylene-17β-acetoxyandrosta-4,6-dien-3-one, 17α-methyl-17β-acetoxyandrosta-4,6-dien-3-one and the like.

The thiocarboxylic acids to be added to the steroidal 4,6-dien-3-ones include thioacetic acid, thiopropionic acid, thiobenzoic acid and the like. The amount of the thiocarboxylic acid to be used is in the range of 1.1 to 20 moles, preferably 1.5 to 7 moles, per mole of the steroidal 4,6-dien-3-one.

The therapeutically useful spironolactone can be obtained by the reaction of 17-hydroxy-3-oxo-17α-pregna-4,6-diene-21-carboxylic acid γ-lactone with thioacetic acid. The strong acids which are used in accordance with the process of this invention are intended to include those acids having higher acidity than that of the thiocarboxylic acid. Exemplary of such strong acids are sulfonic acids such as methanesulfonic acid, ethanesulfonic acid, p-toluenesulfonic acid and trifluoromethanesulfonic acid: halo-substituted carboxylic acids such as trifluoroacetic acid and trichloroacetic acid; and inorganic acids such as sulfuric acid, nitric acid, perchloric acid and hydrochloric acid. The most preferred strong acid is p-toluenesulfonic acid. The concentration of the strong acid is in the range of 0.6 to 0.003 mole/liter, preferably 0.1 to 0.006 mole/liter.

The addition reaction of a thiocarboxylic acid to a steroidal 4,6-dien-3-one may be carried out at a temperature of 10° to 120° C., preferably 30° to 100° C. and more preferably 50° to 85° C.

The reaction involved in the process of this invention is carried out in the presence of a neutral organic solvent. Suitable solvents include hydrocarbon solvents, ethers and the like. Especially preferred solvents are benzene, tetrahydrofuran and dioxane. As previously mentioned, in the prior art processes in which no strong acid is added, the reaction rate is extremely low and it is very difficult to obtain a conversion of 95% or higher. Moreover, if the reaction is carried out with an increased amount of a thiocarboxylic acid or for a prolonged period of time in order to increase the reaction rate or conversion, the prior art processes suffer the disadvantage that large amounts of by-products are formed in addition to the 7-acylthio derivatives.

In accordance with the process of this invention, the addition of the strong acid makes possible a higher reaction rate with the avoidance of formation of by-products.

The 7-acylthio derivatives are a mixture of the 7α-acylthio derivative and the 7β-acylthio derivative, from which the therapeutically active 7α-acylthio derivative can readily be isolated by a simple purification procedure such as recrystallization. As the therapeutically inactive 7β-acylthio derivative is readily converted to the starting steroidal 4,6-dien-3-one in a high yield under basic conditions, the avoidance of the formation of by-products makes the process of this invention economically attractive in the sense that the yield of the desired 7α-acylthio derivative is increased.

An additional advantage of the process of this invention which was entirely unexpected is that the 7β-acylthio derivative is isomerized to the 7α-acylthio derivative in the presence of a strong acid.

The following examples, comparative examples and reference examples are presented to further illustrate this invention but are not intended to limit the scope thereof.

EXAMPLE 1

A mixture of 15.0464 g (44.19 mmole) of 17-hydroxy-3-oxo-17α-pregna-4,6-diene-21-carboxylic acid γ-lactone, 45 ml of benzene and 0.5962 g (3.46 mmole) of p-toluenesulfonic acid is heated to 75° C. in an atmosphere of nitrogen. To this mixture 9.00 g (118.3 mmole) of thioacetic acid is added and stirring is continued for two hours. Upon cooling to room temperature, 105 ml of aqueous saturated sodium bicarbonate solution is added and stirring is continued for an additional 30 minutes. The benzene layer is separated and concentrated, yielding 21.099 g of white crystals. The liquid-chromatographic analysis of these crystals shows that they contain 16.992 g (40.79 mmole; 92.3 mol % yield) of 7α-acetylthio-17-hydroxy-3-oxo-17α-pregn-4-ene-21-carboxylic acid γ-lactone and 1.381 g (3.31 mmole; 7.5 mol % of 7β-acetylthio-17-hydroxy-3-oxo-17α-pregn-4-ene-21-carboxylic acid γ-lactone.

COMPARATIVE EXAMPLE 1

A mixture of 5.00 g (14.7 mmole) of 17-hydroxy-3-oxo-17α-pregna-4,6-diene-21-carboxylic acid γ-lactone and 15 ml of benzene is heated to 75° C. in an atmosphere of nitrogen. To the mixture is added 3.0 g of thioacetic acid and stirring is continued for two hours. Upon cooling to room temperature, 30 ml of aqueous saturated sodium bicarbonate solution is added and stirring is continued for an additional 30 minutes. Thereafter the benzene layer is separated. According to the liquid-chromatographic analysis of the benzene solution, 1.617 g (3.88 mmole; 26.4% yield) of 7α-acetylthio-17-hydroxy-3-oxo-17α-pregn-4-ene-21-carboxylic acid γ-lactone and 0.270 g (0.646 mmole; 4.4% yield) of 7β-acetylthio-17-hydroxy-3-oxo-17α-pregn-4-ene-21-carboxylic acid γ-lactone are obtained, while 3.183 g (9.35 mmole; 63.6% recovery) of the starting 17-hydroxy-3-oxo-17α-pregna-4,6-diene-21-carboxylic acid γ-lactone is recovered.

EXAMPLE 2

To a mixture of 5.0 g of 17-hydroxy-3-oxo-17α-pregna-4,6-diene-21-carboxylic acid γ-lactone, 15 ml of tetrahydrofuran and 0.20 g of p-toluenesulfonic acid which has been heated at 60° C. in an atmosphere of nitrogen, 3.0 g of thioacetic acid is added and stirring is continued for an hour. Upon cooling, the resulting reaction solution is subjected to liquid-chromatographic analysis. It is found that 7α- and 7β-acetylthio-17-hydroxy-3-oxo-17α-pregn-4-ene-21-carboxylic acid γ-lactones are obtained in yields of 78.8 mol % and 16.8 mol %, respectively, and that 4.0% of the starting 17-hydroxy-3-oxo-17α-pregna-4,6-diene-21-carboxylic acid γ-lactone is recovered.

COMPARATIVE EXAMPLE 2

The procedure of example 2 is repeated except that the addition of p-toluenesulfonic acid is omitted. The analysis shows that 7α- and 7β-acetylthio-17-hydroxy-3-oxo-17α-pregn-4-ene-21-carboxylic acid γ-lactones are obtained in yields of 54.9 mol % and 12.6 mol %, respectively, and that 27.5 mol % of the starting 17-hydroxy-3-oxo-17α-pregna-4,6-diene-21-carboxylic acid γ-lactone is recovered.

EXAMPLE 3

The reaction is conducted in exactly the same manner as described in Example 1, while the change of products with the lapse of reaction time is investigated. The results are summarized in Table 1 below.

Table 1

| Reaction time (hr) | % Conversion | Yield of product (%) | |
|---|---|---|---|
| | | α-SPL* | β-SPL** |
| 0.5 | 96.5 | 82.0 | 14.5 |
| 1.5 | 98.5 | 87.0 | 11.0 |
| 2.0 | 100.0 | 92.3 | 7.5 |

*α-SPL: 7α-Acetylthio-17-hydroxy-3-oxo-17β-pregn-4-ene-21-carboxylic acid γ-lactone
**β-SPL: 7β-Acetylthio-17-hydroxy-3-oxo-17α-pregn-4-ene-21-carboxylic acid γ-lactone It is apparent that the 7β-acetylthio derivative is converted to the 7α-acetylthio derivative.

REFERENCE EXAMPLE 1

To a solution of 1.827 g (4.39 mmole) of 7α-acetylthio-17-hydroxy-3-oxo-17α-pregn-4-ene-21-carboxylic acid γ-lactone, 1.3507 g (3.24 mmole) of 7β-acetylthio-17-hydroxy-3-oxo-17α-pregn-4-ene-21-carboxylic acid γ-lactone and 0.0949 g (0.28 mmole) of 17-hydroxy-3-oxo-17α-pregna-4,6-diene-21-carboxylic acid γ-lactone dissolved in 312 ml of methanol, 19 ml of 1 N sodium hydroxide solution is added and the mixture is stirred for 3 hours at 40° C. After the hydrolysis reaction, the reaction mixture is neutralized with aqueous hydrochloride. Methanol is then distilled off and the residue is extracted with benzene. The benzene extract is concentrated to give 2.7190 g of crystals. The liquid-chromatographic analysis of these crystals shows that they contain 2.4091 g (7.06 mmole; 89.3% recovery) of 17-hydroxy-3-oxo-17α-pregna-4,6-diene-21-carboxylic acid γ-lactone.

REFERENCE EXAMPLE 2

To a solution of 5.00 g (14.7 mmole) of 17-hydroxy-3-oxo-17α-pregna-4,6-diene-21-carboxylic acid γ-lactone in 15 ml of methanol is added 3.00 g of thioacetic acid, and the mixture is reacted for 2 hours at 20° C. The above procedure is repeated, except that the reaction temperature is 40° C. or 60° C. The relationship between reaction temperature and composition of the product is shown in Table 2 below. It can be seen from this table that the formation of approximately 10% by-products whose structure is unknown is unavoidable.

Table 2

| Reaction temp. (°C.) | CRN* (%) | α-SPL** (%) | β-SPL** (%) | By-products (%) |
|---|---|---|---|---|
| 20 | 1.3 | 75.2 | 15.1 | 8.4 |
| 40 | 0.3 | 78.3 | 11.5 | 9.9 |
| 60 | 0.0 | 88.4 | 3.7 | 7.9 |

*CRN: 17-Hydroxy-3-oxo-17α-pregna-4,6-diene-21-carboxylic acid γ-lactone.
**α-SPL, β-SPL: See the footnote of Table 1.

Having now fully described the invention, it will be apparent to one of ordinary skill in the art that many changes and modifications can be made thereto without departing from the spirit or scope of the invention as set forth herein.

What is claimed as new and intended to be covered by Letters Patent of the United States is:

1. In a process for producing a steroidal 7α-acylthio-4-en-3-one by the addition of a thiocarboxylic acid to a steroidal 4,6-dien-3-one, the improvement which comprises effecting the reaction in the presence of a strong acid in a neutral organic solvent.

2. The process of claim 1, wherein said steroidal 4,6-dien-3-one is 17-hydroxy-3-oxo-17α-pregna-4,6-diene-21-carboxylic acid α-lactone.

3. The process of claim 1, wherein said thiocarboxylic acid is thioacetic acid.

4. The process of claim 1, wherein said strong acid is p-toluenesulfonic acid.

5. The process of claim 1, wherein said neutral organic solvent is benzene, tetrahydrofuran or dioxane.

6. The process of claim 5, wherein said solvent is benzene.

7. The process of claim 1, wherein the concentration of said strong acid is in the range of from 0.003 to 0.6 mole/liter.

8. The process of claim 1, wherein said reaction is effected at a temperature of from 10° to 120° C.

9. The process of claim 8, wherein said temperature is from 50° to 85° C.

10. The process of claim 1, wherein the amount of said thiocarboxylic acid is in the range of from 1.1 to 20 moles per mole of said steroidal 4,6-dien-3-one.

11. The process of claim 10, wherein said amount is in the range of from 1.5 to 7 moles per mole of said steroidal 4,6-dien-3-one.

12. The process according to claim 1, wherein the neutral organic solvent is selected from the group consisting of hydrocarbons and ethers.

* * * * *